US012127865B2

(12) United States Patent
Choi

(10) Patent No.: US 12,127,865 B2
(45) Date of Patent: Oct. 29, 2024

(54) COMPLEX SPINE-INSPECTION SUPPORT APPARATUS CAPABLE OF MULTI POSTURE CORRECTION

(71) Applicant: Hong Hee Choi, Seoul (KR)

(72) Inventor: Hong Hee Choi, Seoul (KR)

( * ) Notice: Subject to any disclaimer, the term of this patent is extended or adjusted under 35 U.S.C. 154(b) by 407 days.

(21) Appl. No.: 17/466,921

(22) Filed: Sep. 3, 2021

(65) Prior Publication Data

US 2021/0393219 A1 Dec. 23, 2021

Related U.S. Application Data

(63) Continuation of application No. PCT/KR2020/002587, filed on Feb. 23, 2020.

(30) Foreign Application Priority Data

Mar. 13, 2019 (KR) ........................ 10-2019-0028982

(51) Int. Cl.
*A61B 6/04* (2006.01)
*A47C 31/00* (2006.01)
(Continued)

(52) U.S. Cl.
CPC ............ *A61B 6/0478* (2013.01); *A47C 31/00* (2013.01); *A61B 5/4566* (2013.01);
(Continued)

(58) Field of Classification Search
CPC ............... Y10T 24/44034; Y10T 24/23; Y10T 24/44017; Y10T 24/34; Y10T 24/44077;
(Continued)

(56) References Cited

U.S. PATENT DOCUMENTS 2,262,271 A * 11/1941 De Camp ............ A61H 1/0222
602/36
3,434,165 A * 3/1969 Keane .................... A61G 7/008
5/624

(Continued)

FOREIGN PATENT DOCUMENTS

KR 200294464 Y1 11/2002
KR 20100122299 * 5/2009 ............. A61H 39/04
(Continued)

OTHER PUBLICATIONS

International Search Report of PCT/KR2020/002587, May 29, 2020, English translation of abstract.

*Primary Examiner* — Justin C Mikowski
*Assistant Examiner* — Madison Emanski
(74) *Attorney, Agent, or Firm* — STIP Law Group, LLC

(57) ABSTRACT

The present invention is a complex spine-inspection support apparatus capable of multi-posture correction, which can apply various acting forces in a longitudinal direction of a spine while stably maintaining a patient's posture, can transmit a constant bending force to the left and right, thus facilitating accurate and various inspections, and can observe a spinal disc ligament varying depending on a posture. The present apparatus includes an apparatus bed configured to allow a patient to lie on an upper surface thereof; a lower-body support unit configured to allow a leg region to be seated in an "L" shape; a lower-body support unit driving means; a leg holder; an upper-body support means; and a control panel for an operation of the lower-body support unit driving means.

2 Claims, 5 Drawing Sheets

(51) Int. Cl.
*A61B 5/00* (2006.01)
*A61F 5/042* (2006.01)
*A61G 13/00* (2006.01)
*A61H 1/00* (2006.01)
*A61H 1/02* (2006.01)
*A63B 23/00* (2006.01)

(52) U.S. Cl.
CPC ............ *A61B 6/0442* (2013.01); *A61F 5/042* (2013.01); *A61G 13/009* (2013.01); *A61H 1/008* (2013.01); *A61H 1/02* (2013.01); *A61H 1/0222* (2013.01); *A61H 1/0292* (2013.01); *A61B 2560/0266* (2013.01); *A61H 2201/0142* (2013.01); *A61H 2203/0456* (2013.01); *A63B 2023/006* (2013.01)

(58) Field of Classification Search
CPC ......... Y10T 24/44547; Y10T 29/49826; A61B 6/0478; A61B 6/0442; A61B 2560/0266; A61B 6/035; A61B 6/0421; A61B 5/00; A61B 5/055; A61B 5/4561; A61B 5/4566; A61B 6/0407; A61B 5/0035; A61F 5/05; A61F 5/3769; A61F 5/042; A61F 5/0102; A61F 5/04; A61G 13/1285; A61G 13/1295; A61G 13/122; A61G 13/123; A61G 13/1245; A61G 7/065; A61G 13/12; A61G 13/009; A61G 13/08; A61G 13/1225; A61H 1/0218; A61H 1/0292; A61H 1/0222; A61H 1/02; A61H 2203/045; A61H 2201/0142; A61H 2203/0431; A61H 2201/0192; A61H 2201/1207; A61H 2201/1246; A61H 1/008; A61H 2203/0456; A61H 2201/163; A63B 2023/006; A63B 23/0238; A63B 21/4035; A47C 21/00; A47C 31/00; Y10S 5/937
USPC ............................................................ 5/621
See application file for complete search history.

(56) References Cited

U.S. PATENT DOCUMENTS

| | | | | |
|---|---|---|---|---|
| 5,192,306 | A | * | 3/1993 | Scott .................... A61G 13/009 5/608 |
| 5,217,488 | A | * | 6/1993 | Wu ....................... A61H 1/0218 606/241 |
| 2008/0150535 | A1 | | 6/2008 | Hoogeveen |

FOREIGN PATENT DOCUMENTS

| | | | | |
|---|---|---|---|---|
| KR | 100922278 B1 | | 10/2009 | |
| KR | 20110093180 | * | 2/2010 | ........... A61H 1/0292 |
| KR | 20130070755 | * | 12/2011 | ........... A61H 1/0222 |
| KR | 20120060798 | * | 4/2012 | ........... A61H 1/0292 |
| KR | 20130070755 A | | 6/2013 | |
| KR | 101332019 B1 | | 11/2013 | |
| KR | 20140057504 A | | 5/2014 | |
| KR | 20170085756 A | | 7/2017 | |
| KR | 20180055087 A | | 5/2018 | |
| KR | 20190018265 A | | 2/2019 | |

* cited by examiner

COMPLEX SPINE-INSPECTION SUPPORT APPARATUS CAPABLE OF MULTI POSTURE CORRECTION

CROSS-REFERENCE TO RELATED APPLICATION

This application is a continuation of Application No. PCT/KR2020/002587 filed on Feb. 23, 2020, which in turn claims the benefit of Korean Patent Application No. 10-2019-0028982 filed on Mar. 13, 2019, the disclosures of which are incorporated by reference into the present application.

BACKGROUND

(a) Technical Field

The present invention relates to a complex spine-inspection support apparatus capable of multi-posture correction. More particularly, the present invention relates to a complex spine-inspection support apparatus capable of multi-posture correction, which can apply various acting forces in a longitudinal direction of a spine while stably maintaining a patient's posture, can transmit a constant bending force to the left and right, thus facilitating accurate and various inspections, and can observe a vertebral body and a spinal disc ligament varying depending on a posture.

(b) Background Art

Medical images used to diagnose a patient are typically classified into a structural image and a functional image. The structural image means the structure and anatomical image of a human body, and the functional image is to directly or indirectly image functional information on the cognition and sensory function of the human body. In this case, CT, MRI, etc. are technology corresponding to structure imaging technology.

Generally, a CT (Computed Tomography) apparatus is a type of diagnostic inspection equipment that reconstructs the structure of the human body into a cross-section using X-rays and a computer. This is a good inspection method for observing the location and shape of a lesion because the anatomical change of body organs is relatively easily and accurately reflected.

Furthermore, this is an apparatus that finds and analyzes lesions using the characteristics of an electric field, and creates a three-dimensional image by taking images while rotating X-rays. The CT apparatus is basically implemented using X-rays, and is equipment that takes an image while the X-rays turning around a lying patient. By reconstructing X-ray information obtained through photographing into an image on the computer, the section of a painful site is clearly shown as if a radish were cut with a knife. In a general X-ray image, it is possible to accurately diagnose internal organs or anatomically complex structures that are not visible due to overlapping.

As such, the CT apparatus is advantageous in that a scanning operation may be performed within a short period of time, so that a clear image can be obtained without motion artifacts caused by the movement of the human body such as breathing. Furthermore, when injecting a drug called a contrast medium, which is often used to take an image of a blood vessel or to identify the characteristics of tissue, the scanning operation is performed at the time when the concentration in the blood vessel is highest, so that CT angiography may be performed and the amount of contrast medium may be reduced. Although such a CT apparatus is useful for diagnosing most diseases, including the evaluation of a fracture patient, this is evaluated to be useful for brain diseases, head and neck tumors, lung cancer, tumors of various digestive organs, and liver cancer.

Currently, a common MRI apparatus that is most widely used in clinical care and research as an anatomical image is an apparatus that finds and analyzes a lesion using the force of a magnetic field. Furthermore, unlike the CT apparatus, the MRI apparatus detects anatomical changes in a human body using the principle of Nuclear Magnetic Resonance (NMR). Thus, the MRI apparatus is harmless to the human body because it is not exposed to radiation, and can obtain high-resolution anatomical information compared to other imaging equipment, and allows multi-planar imaging and 3D imaging.

For this reason, the MRI apparatus is very useful for photographing soft tissue such as muscles, ligaments, brain nervous system, and tumors. Recently, the MRI apparatus is widely used to identify the range of soft tissue cancers such as breast cancer, liver cancer, ovarian cancer, and cervical cancer.

Moreover, in the case of cerebrovascular or spine nerves, the MRI apparatus may see a blood vessel and a spinal canal without using a contrast medium, so side effects of the contrast medium may be avoided. In the case of a patient with spine disease, X-ray inspection is basically performed. To improve accuracy, additional inspections such as CT and MRI are performed. To accurately observe a spinal canal and spine nerve bundles in multiple directions, MRI-Myelogram is performed.

Furthermore, the MRI apparatus is an image diagnosis device that may obtain the tomographic shape of the body using the signal of the magnetization of atomic nuclei in a living body. The reason why an image in the living body may be obtained using magnetism and high frequency is because the living body is composed of hydrogen molecules that are affected by countless magnets. 70% of the living body is composed of water, and each water molecule contains one hydrogen atom, which acts as a very small magnet.

Such a CT apparatus or MRI apparatus is equipped with a patient table for a patient to take a stable posture and to take an image. The patient table uses a patient holding device that may improve an image while maintaining the stable posture by limiting a patient's will.

As the conventional patient holding device, a device for fixing a patient holding belt with a groove and a detachable device are used. However, the devices are problematic in that a patient is not accurately held, so that a photographed image is deteriorated, a photographing operation should be performed again, and thereby the devices are uneconomical.

Furthermore, it is impossible to move the belt according to a patient's position and region, so the belt may not comfortably hold a patient with a different body condition, resulting in reduced comfort.

In particular, the structure and shape of the vertebral body, disc and ligament are changed according to the load caused by gravity and body weight and several posture changes.

However, because of the characteristics of the general MRI apparatus, inspection may be done while a patient lying down comfortably. However, it is difficult to accurately observe a pain trigger point, such as a site or location of a different disease for each patient, and an area where the nerve is compressed.

In order to solve the problems, a standing MRI or a loading device has been proposed. This is problematic in that purchase, installation and maintenance costs are significantly increased, it is difficult to observe a change in the disc due to an unstable posture, knee-ankle pain, and short-time inspection, and this is only used for inspection that applies a load to the spine.

PRIOR ART DOCUMENTS

Patent Documents

Patent Document 1: Korean Patent No. 10-1332019 (Nov. 15, 2013)
Patent Document 2: Korean U.M. Registration No. 20-0294464 (Oct. 28, 2002)
Patent Document 3: Korean Patent Laid-Open Publication No. 10-2017-0085756 (Jul. 25, 2017)
Patent Document 4: Korean Patent Laid-Open Publication No. 10-2014-0057504 (May 13, 2014)

SUMMARY OF THE INVENTION

The present invention has been made in an effort to solve the above-described problems associated with prior art and to provide a complex spine-inspection support apparatus capable of multi-posture correction, which can apply various acting forces in a longitudinal direction of a spine while stably maintaining a patient's posture, and can transmit a constant bending force to the left and right, thus facilitating accurate and various inspections.

Also, the present invention provides a complex spine-inspection support apparatus capable of multi-posture correction, which is intended to observe a vertebral body and a spinal disc ligament varying depending on a posture, thus providing a novel inspection method and inspection type.

According to one aspect of the invention, the present invention provides a spine-inspection support apparatus for supporting a patient's posture in equipment including a spine inspection, the apparatus including an apparatus bed configured to allow a patient to lie on an upper surface thereof; a lower-body support unit movably provided on a first end of the apparatus bed in a longitudinal direction of the apparatus bed to come into close contact with a patient's buttocks and configured to allow a leg region to be seated in an "L" shape; a lower-body support unit driving means provided on the first end of the apparatus bed to linearly move the lower-body support unit; leg holding means provided on the lower-body support unit to hold the patient's leg region; an upper-body support means provided on the apparatus bed to support and hold the patient's upper body; and a control panel for controlling an operation of the lower-body support unit driving means.

Further, the apparatus bed may include on an upper surface thereof a non-magnetic bed plate that is adjustable in length, the lower-body support unit may include a longitudinal support plate part that is in close contact with the patient's buttock region and thigh region, and a transverse support plate part that extends from an upper end of the longitudinal support plate part to be bent to a side, thus allowing the patient's calf region to be seated thereon, and the lower-body support unit driving means may include a support bracket that is installed at the first end of the apparatus bed, and a hydraulic cylinder that is secured at a first end thereof to the support bracket, is coupled at a second end thereof to a rear surface of the transverse support plate part of the lower-body support unit, and is controlled by the control panel.

The upper-body support means may include a flank holding means that is provided on a first side of the apparatus bed to hold a patient's flank region, and a shoulder holding means that is provided on an upper end of the apparatus bed to hold a patient's shoulder region.

Furthermore, each of the flank holding means and the shoulder holding means may include a rotating shaft provided on a predetermined portion of each edge of the apparatus bed, and a roller-type support member rotatably coupled to the rotating shaft, and may further include a movement guide means to move each of the flank holding means and the shoulder holding means to a predetermined location, The movement guide means may include a guide rail formed along the edge of the apparatus bed, and a rolling member provided on a lower end of the rotating shaft to be movable along the guide rail.

The apparatus may further include a cushioning-force providing means provided on each of the flank holding means and the shoulder holding means to provide a cushioning force of the holding means to the patient.

In addition, the cushioning-force providing means may be configured such that the rotating shaft is composed of a bearing, a gap of a predetermined size is formed between the rotating shaft and the roller-type support member, and a tension spring is provided in the gap to absorb an external force transmitted to the roller-type support member.

Further, the tension spring may include a contact part that protrudes to be in close contact with a portion of an inner surface of a coupling hole of the roller-type support member, an action part that extends from each of opposite sides of the contact part, is bent inwards, and performs a tension action for absorbing external force, and a compression part that extends from the action part and is seated on a portion of an outer surface of the rotating shaft to prevent it from being removed from the rotating shaft.

The apparatus may further include a posture display means configured to display and monitor the patient's seating posture, the posture display means may include a camera module that is provided on a side of the apparatus bed to photograph the patient's upper body, and a display module that is provided on a side of the apparatus bed at which the patient's head region is located, and displays an image photographed by the camera module. A center line of the apparatus bed may be displayed on the display module to overlap a patient's image that is photographed and displayed.

As is apparent from the above description, the complex spine-inspection support apparatus capable of multi-posture correction of the present invention is advantageous in that a patient can be stably maintained even in various postures, thus facilitating diagnosis and observation.

Furthermore, it is possible to apply various acting forces in a longitudinal direction of a spine, and to transmit a constant bending force to the left and right, thus facilitating accurate and various inspections.

In addition, the present invention is intended to observe a vertebral body and a spinal disc ligament varying depending on a posture, thus providing a novel inspection method and inspection type. This is a very useful invention that can greatly contribute to the development and revitalization of industries related to the development of medical devices as well as medical technologies such as related treatment and diagnosis, according to the above-described effects.

DETAILED DESCRIPTION

Figure 1:
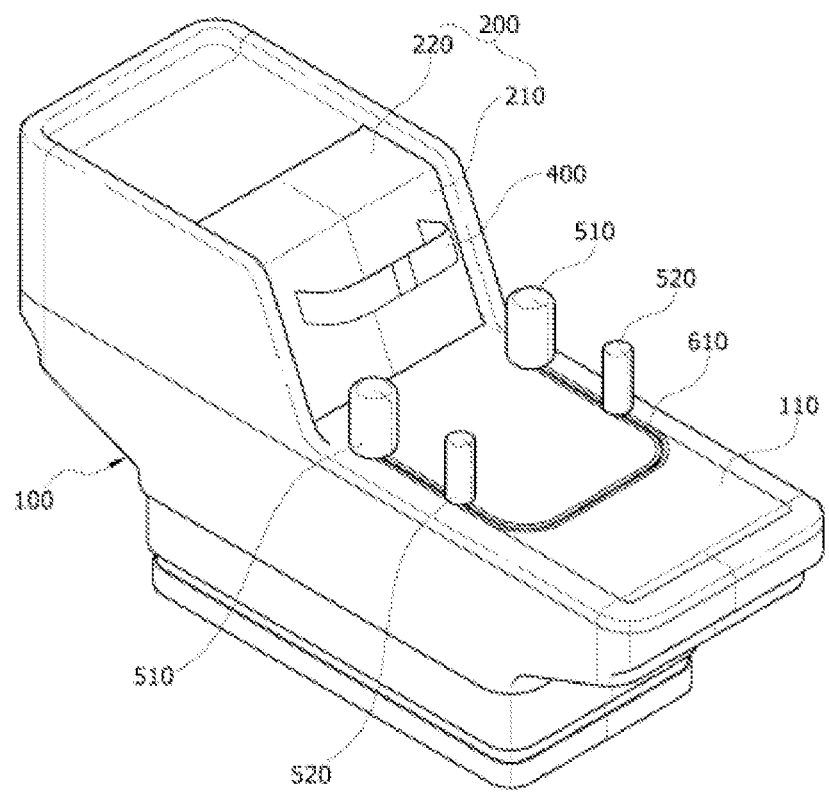
FIG. 1 is a perspective view showing an external structure of a complex spine-inspection support apparatus capable of multi-posture correction according to the present invention.

Hereinafter, preferred embodiments of the present invention will be described in detail with reference to the accompanying drawings such that those skilled in the art can easily practice the present invention.

First, it is to be noted that like reference numerals refer to like parts throughout various figures and embodiments of the present invention. Furthermore, when it is determined that the detailed description of known configurations and functions makes the gist of the present invention obscure, the detailed description will be omitted herein.

Figure 2:
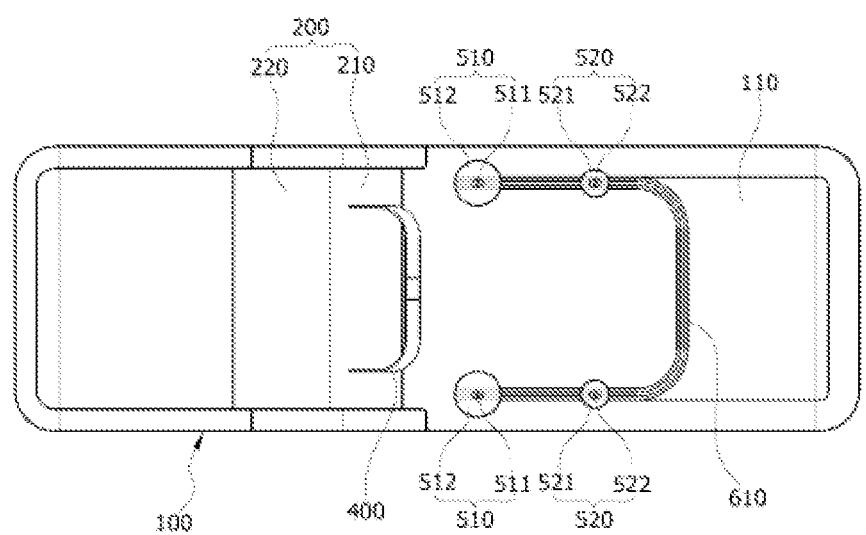
FIG. 2 is a plan view showing a planar structure of the complex spine-inspection support apparatus capable of multi-posture correction according to the present invention.
Figure 3:
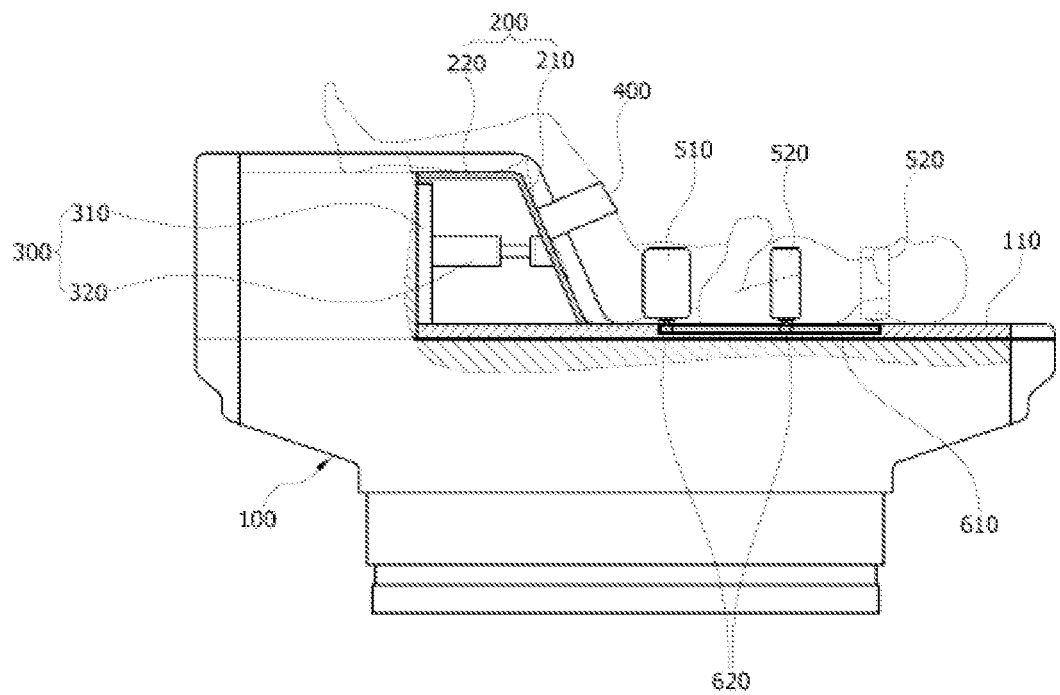
FIG. 3 is a diagram showing the use of the complex spine-inspection support apparatus capable of multi-posture correction according to the present invention.
Figure 4A:
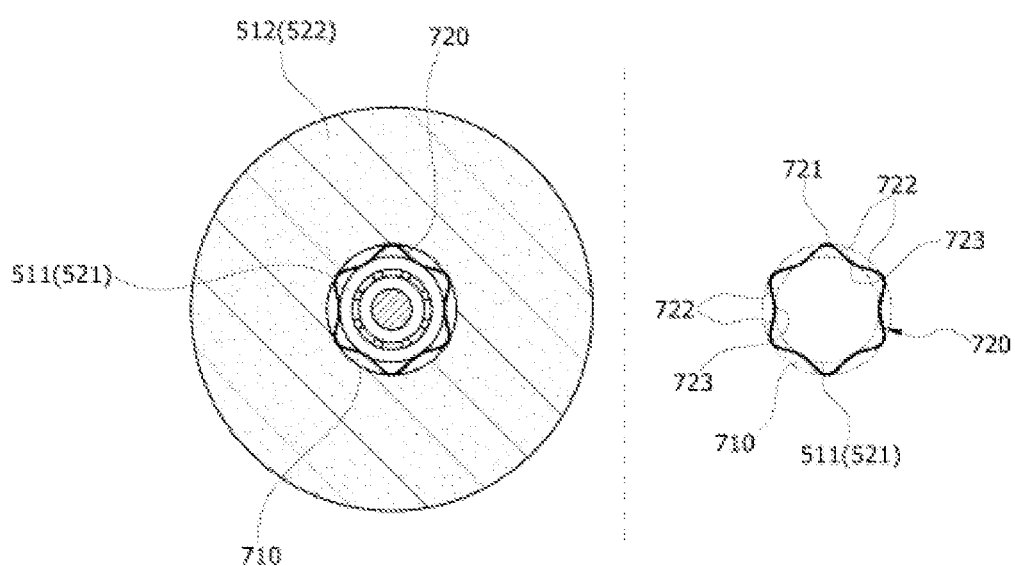
FIG. 4A, FIG. 4B, FIG. 4C, FIG. 4D and FIG. 4E are sectional views showing the operational relationship of a cushioning-force providing means, in the complex spine-inspection support apparatus capable of multi-posture correction according to the present invention.
Figure 4B:
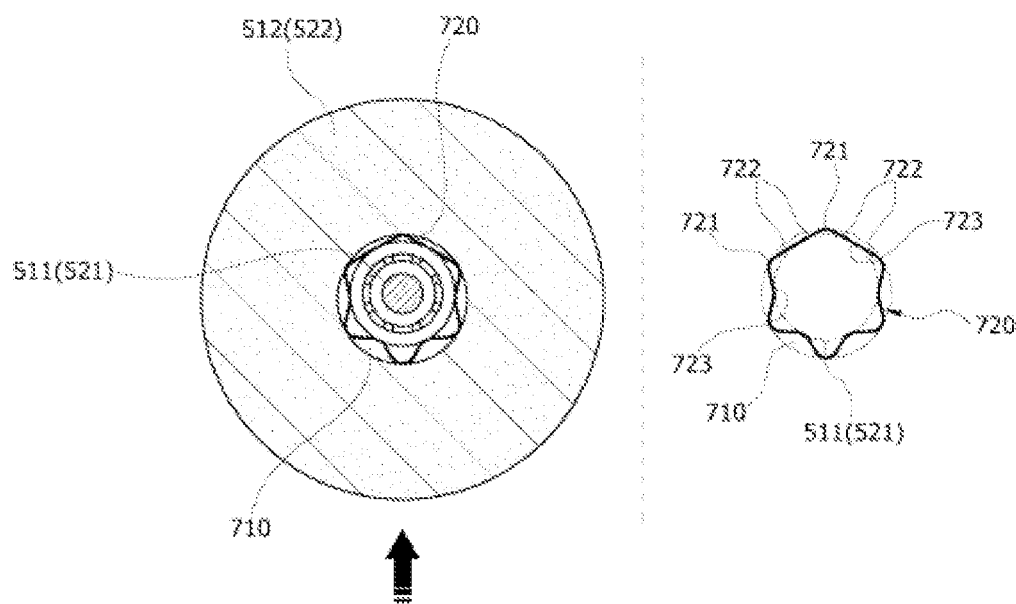
Figure 4C:
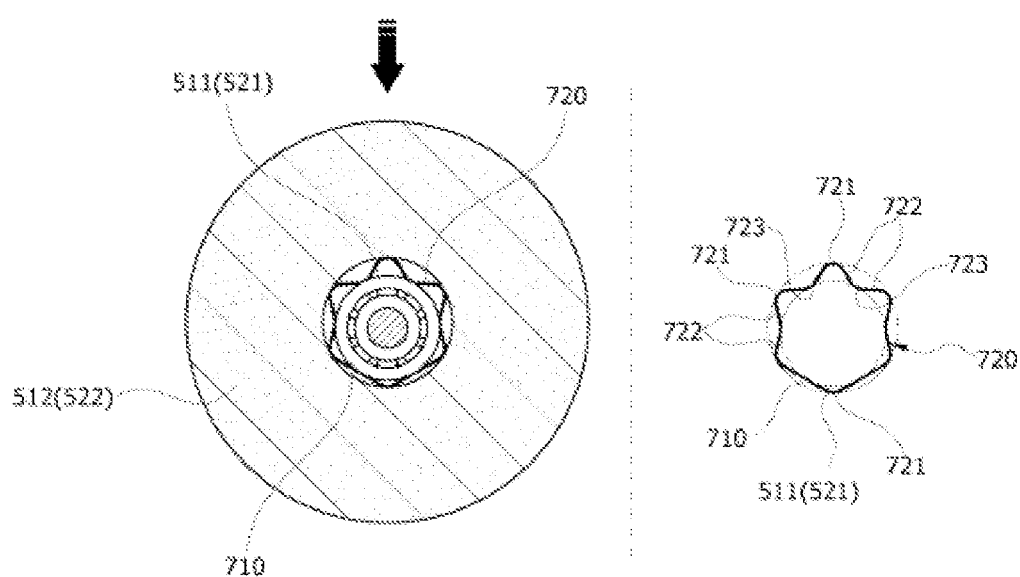
Figure 4D:
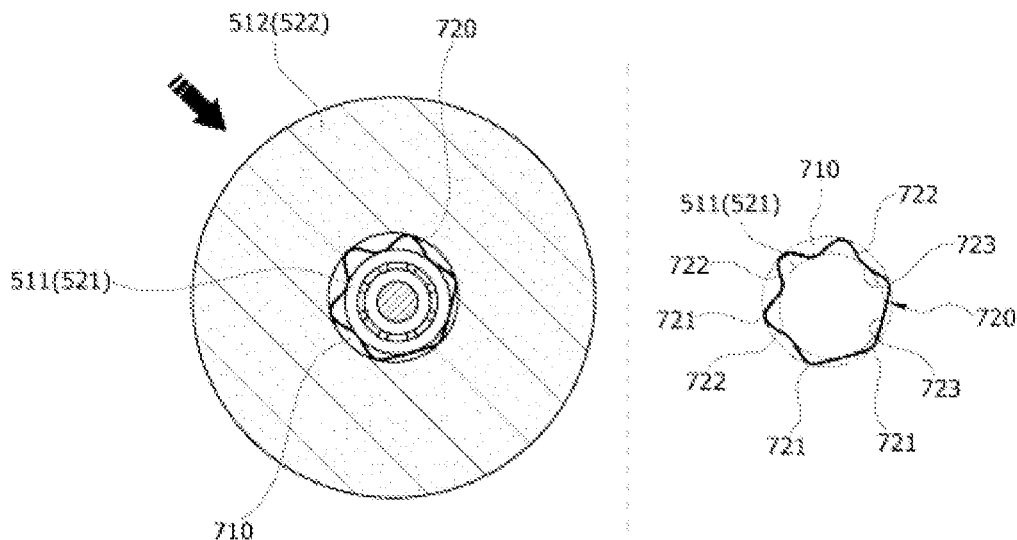
Figure 4E:
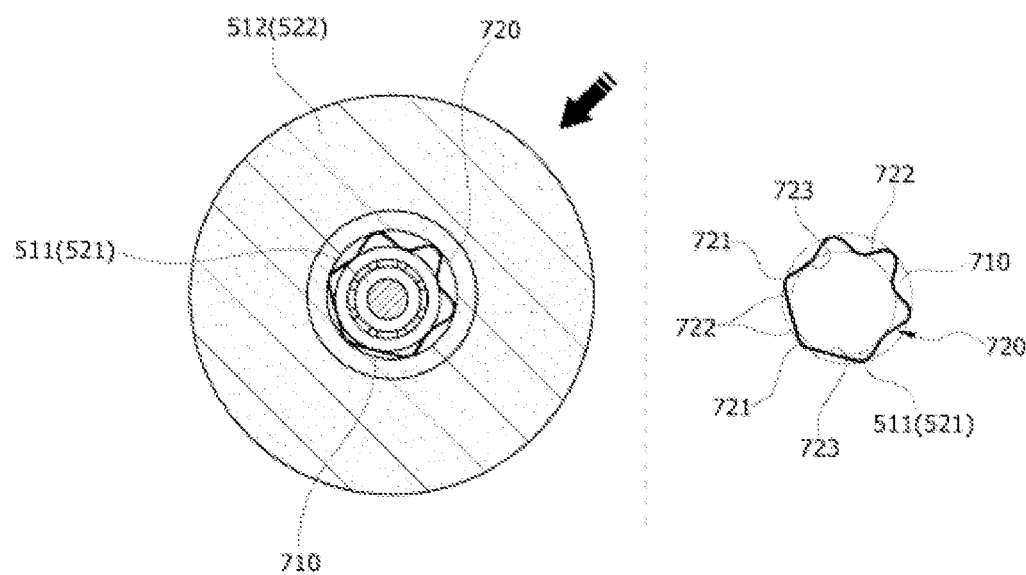
Figure 5:
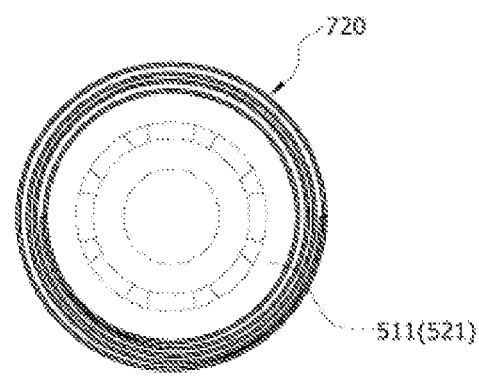
FIG. 5 is a planar sectional view showing another embodiment of a cushioning-force providing means, in the complex spine-inspection support apparatus capable of multi-posture correction according to the present invention.

FIG. 1 is a perspective view showing an external structure of a complex spine-inspection support apparatus capable of multi-posture correction according to the present invention, FIG. 2 is a plan view showing a planar structure of the complex spine-inspection support apparatus capable of multi-posture correction according to the present invention, FIG. 3 is a diagram showing the use of the complex spine-inspection support apparatus capable of multi-posture correction according to the present invention, FIGS. 4A to 4E are sectional views showing the operational relationship of a cushioning-force providing means, in the complex spine-inspection support apparatus capable of multi-posture correction according to the present invention, and FIG. 5 is a planar sectional view showing another embodiment of a cushioning-force providing means, in the complex spine-inspection support apparatus capable of multi-posture correction according to the present invention.

As shown in FIGS. 1 to 3, the complex spine-inspection support apparatus capable of multi-posture correction according to the present invention is a spine-inspection support apparatus for supporting a patient's posture in equipment including a spine inspection. The apparatus includes an apparatus bed 100 that is configured to allow a patient to lie on an upper surface thereof, a lower-body support unit 200 that is movably provided on a first end of the apparatus bed 100 in a longitudinal direction of the apparatus bed 100 to come into close contact with a patient's buttocks and is configured to allow a leg region to be seated in an "L" shape, a lower-body support unit driving means 300 that is provided on the first end of the apparatus bed 100 to linearly move the lower-body support unit 200, a leg holding means 400 that is provided on the lower-body support unit 200 to hold a patient's leg region, an upper-body support means that is provided on the apparatus bed 100 to support and hold a patient's upper body, and a control panel (not shown) that controls the operation of the lower-body support unit driving means 300.

The apparatus bed 100 is provided with a bed plate 110 that is configured to allow a patient to lie on an upper surface thereof. Here, the bed plate 110 is preferably formed of a non-magnetic metal plate that minimizes friction on a patient's back to easily slide thereon when the lower-body support unit 200 is linearly moved by the lower-body support unit driving means 300.

Furthermore, a non-metallic material is more preferably provided on a patient's back.

The metal plate forming the apparatus bed 100 may be configured to be stretchable in a longitudinal direction. Thus, this may be adjusted according to a patient's height, and is also configured to be associated with the upper-body support means that will be described below.

Although will be described later, components constituting the upper-body holding means are provided on an edge of the apparatus bed 100.

Next, the lower-body support unit 200 may be composed of an "L"-shaped seat member that is movably provided on the first end of the apparatus bed 100 in the longitudinal direction of the apparatus bed 100 to come into close contact with a patient's buttocks and allow the leg region to be seated thereon in an "L" shape. This is not particularly limited as long as this may come into close contact with a patient's buttocks, allows the leg region to be seated thereon in the "L" shape, and may be driven by the lower-body support unit driving means 300.

For example, the lower-body support unit 200 includes a longitudinal support plate part 210 that is in close contact with a patient's buttock region and thigh region, and a transverse support plate part 220 that extends from an upper end of the longitudinal support plate part 210 to one side (rear side) by a predetermined length, thus allowing a patient's calf region to be seated thereon.

Such a lower-body support unit 200 is configured to move forwards or backwards by a predetermined stroke by the lower-body support unit driving means 300 that will be described later.

Next, the lower-body support unit driving means 300 includes a support bracket 310 that is erected on the first end of the apparatus bed 100, and a hydraulic cylinder 320 that is secured at a first end thereof to the support bracket 310, is coupled at a second end thereof to the rear surface of the lower-body support unit 200, and is controlled by the control panel.

Such a hydraulic cylinder 320 is linearly moved by a predetermined amount by the control of the control panel, and is operated to apply a load to a patient's spine or reduce pressure.

Next, the leg holding means 400 may be composed of Velcro band members that are provided on both sides of the longitudinal support plate part 210 of the lower-body support unit 200 to couple ends through a Velcro fastening method, thus fastening a patient's thigh region to the longitudinal support plate part 210.

More preferably, although not shown in the drawings, a configuration for holding a thigh region or a pelvic region may be obviously added to perform an effective holding operation during decompression.

Of course, the leg holding means 400 may adopt various different coupling methods instead of the Velcro band member. The leg holding means is limited thereto as long as it may firmly hold the leg region.

Furthermore, the leg holding means 400 may also be provided on the transverse support plate part 220, and may be composed of Velcro band members to fasten a patient's calf region to the transverse support plate part 220. The leg holding means is not limited thereto.

Next, the upper-body support means includes a flank holding means 510 that is provided on a first side of the apparatus bed 100 to hold a patient's flank region, and a shoulder holding means 520 that is provided on an upper end of the apparatus bed 100 to hold a patient's shoulder region.

The flank holding means 510 includes a rotating shaft 511 that is provided on a predetermined portion of each of opposite edges of the apparatus bed 100, and a roller-type support member 512 that is rotatably coupled to the rotating shaft 511.

Further, the shoulder holding means 520 includes a rotating shaft 521 that is provided on the apparatus bed 100 to be spaced apart from an upper end thereof by a predetermined distance, and a roller-type support member 522 that is rotatably coupled to the rotating shaft 511.

Furthermore, the upper-body support means may further include an armpit holding means (not shown) that is provided on a second side of the apparatus bed 100 to be located in a patient's armpit region and thereby hold the armpit region. However, when the armpit holding means is composed of a movement guide means, the shoulder holding means 520 is moved towards the armpit to serve as the armpit holding means.

In the case of further including the armpit holding means, the armpit holding means may also include a rotating shaft that is provided on a predetermined portion of each of both edges of the apparatus bed 100, and a roller-type support member that is rotatably coupled to the rotating shaft.

On the other hand, the complex spine-inspection support apparatus capable of multi-posture correction according to the present invention may further include a movement guide means that may move the upper-body support means to a predetermined location.

The movement guide means includes a guide rail 610 that is formed along an edge of the apparatus bed 100, and a rolling member (e.g., roller) 620 that is provided on a lower end of each rotating shaft 511, 521, or 531 to be movable along the guide rail 610.

Thus, as described above, the metal plate of the apparatus bed 100 is adjusted to be stretchable according to a patient's height, and each holding means 510 or 520 may move to a predetermined location along the guide rail 610 at a position where the length of the metal plate of the apparatus bed 100 has been adjusted, so that the holding means is adjustable according to a patient's height. Further, each holding means 510 or 520 may move to a predetermined location along the guide rail 610 to be adjustable according to an inspection type or an inspection method (e.g., when it is required to laterally bend a patient).

As such, in the case of having the movement guide means, the shoulder holding means 520 may move towards the armpit region to serve as the armpit holding means. Of course, the present invention may include both the shoulder holding means and the armpit holding means.

Furthermore, the guide rail 610 and the rolling member 620 of the movement guide means may be composed of a rack (it being formed on the metal plate) and a rack gear (it being formed on the rolling member), and a driving motor may be provided on the rack gear to be movably controlled via the control panel, so that it is possible to perform an auto-adjustment operation according to an inspection type or an inspection method.

The complex spine-inspection support apparatus capable of multi-posture correction according to the present invention may further include a cushioning-force providing means that is provided on the upper-body support means to provide the cushioning force of each holding means 510 or 520 to a patient.

FIGS. 4A to 4E are sectional views showing the operational relationship of a cushioning-force providing means, in the complex spine-inspection support apparatus capable of multi-posture correction according to the present invention. As shown in the drawings, the cushioning-force providing means may be configured as follows: each rotating shaft 511 or 521 may be composed of a bearing, a gap 710 of a predetermined size may be formed between each rotating shaft 511 or 521 and each roller-type support member 512 or 522, and a tension spring 720 may be provided in the gap to absorb an external force transmitted to the roller-type support member 512 or 522.

The tension spring 720 may include a contact part 721 that protrudes to be in close contact with a portion of the inner surface of a coupling hole of each roller-type support member 512 or 522, an action part 722 that extends from each of opposite sides of the contact part 721, is bent inwards, and performs a tension action for absorbing external force, and a compression part 723 that extends from the action part 722 and is seated on a portion of the outer surface of each rotating shaft 511 or 521 to prevent it from being removed from the rotating shaft 511 or 521.

Furthermore, FIG. 5 is a planar sectional view showing another embodiment of a cushioning-force providing means, in the complex spine-inspection support apparatus capable of multi-posture correction according to the present invention. The tension spring 720 may have a coil-shaped structure.

The complex spine-inspection support apparatus capable of multi-posture correction according to the present invention may further include a posture display means that may display and monitor a patient's seating posture.

The posture display means may include a camera module that is provided on a side of the apparatus bed 100 to photograph a patient's whole body (or upper body), and a display module that is provided on a side of the apparatus bed 100 at which a patient's head region is located, and displays an image photographed by the camera module. A center line of the apparatus bed may be displayed on the display module to overlap a patient's image that is photographed and displayed.

The posture display means may also be provided in an operator's control room.

Such a posture display means may check whether a patient is located at the center line of the apparatus bed 100 while looking at the display module. Further, when an operator requests a change in posture, the posture is changed while the operator and the patient looking at the display module. Thus, the inspection and the operation may be more accurately performed.

Although not shown in the drawings, an instrument panel, which may monitor values, such as a pressure gauge or a scale, may be more preferably installed on the patient's leg region, and a switch which allows a patient himself or herself to release a fixed pressure may also be provided according to the choice of a user or an installer.

In summary, the complex spine-inspection support apparatus capable of multi-posture correction according to the present invention can make it easy to stably diagnose and observe a patient even in various postures, and can apply various acting forces in the longitudinal direction of the spine, and can transmit a constant bending force to the left or right, thus facilitating accurate and various inspections, and can observe a spinal disc ligament changed depending on a posture, thus providing a novel inspection method and inspection type.

Although not shown in the drawings, a flank pressure support may be easily attached or detached according to a user's choice, and a switch for manually releasing the hydraulic-cylinder pressure may be further provided.

Furthermore, it is apparent that a part of the module, on which a pressure value or a weight value of a hydraulic control unit on a buttock side is displayed, may be installed. According to the present invention, in order to erect the bed in the X-ray inspection, the bed may be separated from the table.

In consideration of the case where a small force is received only by fixing the thigh during decompression, a belt for fixing the pelvis (hip joint) may be added. Although it is shown in the drawings that the flank, armpit, or shoulder support is expressed in a round shape, it may be implemented in a flat elliptical shape according to a user's selection without being limited to the round shape.

Of course, the present invention is not limited to the size of the drawing, and it is apparent that it may be manufactured in a large, medium, or small size for each patient's body size according to the user's choice to be applicable to a very small patient.

Although the present invention was described with reference to specific embodiments shown in the drawings, it is apparent to those skilled in the art that the present invention may be changed and modified in various ways without departing from the scope of the present invention, which is described in the following claims. Therefore, embodiments and drawings disclosed in the present invention are not restrictive but are illustrative, and the technical idea of the present invention is not limited by these embodiments and drawings. Further, the scope of the present invention should be determined by the appended claims rather than by the description preceding them.

| * Description of reference numerals of important parts* | |
|---|---|
| 100: apparatus bed | 110: bed plate |
| 200: lower-body support unit | 210: longitudinal support plate part |
| 220: transverse support plate part | 300: lower-body support unit driving means |
| 310: support bracket | 320: hydraulic cylinder |
| 400: leg holding means | 510: flank holding means |
| 511, 521: rotating shaft | 512, 522: roller-type support member |
| 520: shoulder holding means (or armpit holding means) | |
| 610: guide rail | 620: rolling member |
| 710: gap | 720: tension spring |
| 721: contact part | 722: action part |
| 723: compression part | |

What is claimed is:

1. A complex spine-inspection support apparatus supporting a patient's posture for multi-posture correction, the apparatus comprising:
   an apparatus bed comprising an upper surface and configured to allow the patient to lie on the upper surface;
   a lower-body support unit provided on the apparatus bed, wherein the lower-body support unit is capable of moving in a longitudinal direction of the apparatus bed to contact with the patient's buttocks and is configured to allow a leg region to be seated in an "L" shape, wherein the lower-body support unit comprises a longitudinal support plate part that is in contact with the patient's buttock region and thigh region and a transverse support plate part that is in contact with the patient's calf region and extends from an upper end of the longitudinal support plate part to be bent to a side;
   a lower-body support unit driving means provided below the transverse support plate part and above the apparatus bed, wherein the lower-body support unit driving means is configured to linearly move the lower-body support unit along the longitudinal direction of the apparatus bed;
   a leg holder provided on the longitudinal support plate part and configured to hold the patient's buttock region and thigh region;
   an upper-body support means provided on the apparatus bed and configured to support and hold the patient's upper body; and
   a control panel for operating the lower-body support unit driving means,
   wherein,
   the upper-body support means comprises:
   flank holding means provided on the upper surface of the apparatus bed and configured to hold the patient's flank region;
   shoulder holding means provided on the upper surface of the apparatus bed and configured to hold the patient's shoulder region, wherein the flank holding means are located between the shoulder holding means and the longitudinal support plate part along the longitudinal direction of the apparatus bed; and
   movement guide means provided on the upper surface of the apparatus bed and configured to move each of the flank holding means and the shoulder holding means to a predetermined location on the apparatus bed,
   wherein,
   each of the flank holding means and the shoulder holding means comprises:
   a rotating shaft comprising a bearing;
   a roller support member rotatably coupled to the rotating shaft; and a tension spring located in a gap provided between the rotating shaft and the roller support member and configured to absorb an external force transmitted to the roller support member, the movement guide means comprises a guide rail formed on the apparatus bed and a rolling member provided on the guide rail and below a lower end of the rotating shaft, wherein the rolling member is capable of moving along the guide rail, the tension spring comprises: a contact part that protrudes to be in contact with a portion of an inner surface of a coupling hole of the roller support member; an action part that extends from each of opposite sides of the contact part, is bent inwards, and performs a tension action for absorbing external force; and a compression part that extends from the action part and is seated on a portion of an outer surface of the rotating shaft to prevent the compression part from being removed from the rotating shaft.

2. The complex spine-inspection support apparatus of claim 1,
   wherein the apparatus bed further comprises a non-magnetic bed plate located on the upper surface and the non-magnetic bed platedt is adjustable in length,
   the lower-body support unit driving means comprises:
   a support bracket provided below the transverse support plate part of the lower-body support unit and above the upper surface of the apparatus bed, and a hydraulic cylinder secured at the support bracket, coupled to the longitudinal support plate part of the lower-body support unit, and controlled by the control panel.

\* \* \* \* \*